(12) United States Patent
Kanno et al.

(10) Patent No.: US 11,213,342 B2
(45) Date of Patent: Jan. 4, 2022

(54) SURGICAL INSTRUMENT AND CONNECTOR

(71) Applicant: OLYMPUS CORPORATION, Hachioji (JP)

(72) Inventors: Kenjiro Kanno, Komagane (JP); Tomoyuki Tsuchiya, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 742 days.

(21) Appl. No.: 16/015,847

(22) Filed: Jun. 22, 2018

(65) Prior Publication Data
US 2018/0296238 A1 Oct. 18, 2018

Related U.S. Application Data

(63) Continuation of application No. PCT/JP2016/087275, filed on Dec. 14, 2016.

(30) Foreign Application Priority Data

Dec. 25, 2015 (JP) .............................. JP2015-254881

(51) Int. Cl.
*A61B 18/12* (2006.01)
*A61B 18/14* (2006.01)
(Continued)

(52) U.S. Cl.
CPC ...... *A61B 18/1445* (2013.01); *A61B 17/2812* (2013.01); *A61B 17/320092* (2013.01);
(Continued)

(58) Field of Classification Search
CPC ........ A61B 18/1445; A61B 2017/0046; A61B 2017/2927; A61B 2017/320094; A61B 2018/00178
See application file for complete search history.

(56) References Cited

U.S. PATENT DOCUMENTS

2011/0230875 A1  9/2011 Walberg et al.
2012/0116261 A1* 5/2012 Mumaw ................. A61B 46/10
                                                              601/2
(Continued)

FOREIGN PATENT DOCUMENTS

CN       103796600 A    5/2014
JP       2013046866 A   3/2013
(Continued)

OTHER PUBLICATIONS

Chinese Office Action (and English language translation thereof) dated Jun. 1, 2020 issued in Chinese Application No. 201680074682.8.

(Continued)

*Primary Examiner* — Michael F Peffley
*Assistant Examiner* — Amanda L Zink
(74) *Attorney, Agent, or Firm* — Holtz, Holtz & Volek PC (57) ABSTRACT

A surgical instrument includes: a handpiece; a movable member configured to transmit a driving force to a treating member to treat a subject by moving relatively to the handpiece; and a connector arranged inside the handpiece, and including a strip to apply a pressing force to the movable member. The movable member includes a first conductive portion formed therein. The connector includes a second conductive portion formed on the strip. The second conductive portion abutting against the first conductive portion to connect the movable member and the handpiece electrically. The second conductive portion of the connector is a molded interconnect device constituting a three-dimensional circuit.

9 Claims, 12 Drawing Sheets (51) Int. Cl.
  *A61B 17/32* (2006.01)
  *A61B 17/28* (2006.01)
  *A61B 17/00* (2006.01)
  *A61B 17/29* (2006.01)
  *A61B 18/00* (2006.01)

(52) U.S. Cl.
  CPC ............ *A61B 2017/0046* (2013.01); *A61B 2017/2927* (2013.01); *A61B 2017/320073* (2017.08); *A61B 2017/320082* (2017.08); *A61B 2017/320094* (2017.08); *A61B 2017/320095* (2017.08); *A61B 2018/00178* (2013.01); *A61B 2018/00607* (2013.01); *A61B 2018/00994* (2013.01); *A61B 2018/126* (2013.01); *A61B 2018/1452* (2013.01)

(56) References Cited

U.S. PATENT DOCUMENTS

| | | |
|---|---|---|
| 2012/0253373 A1 | 10/2012 | Young et al. |
| 2013/0096468 A1 | 4/2013 | Rhee et al. |
| 2013/0110155 A1 | 5/2013 | Tsuchiya et al. |
| 2013/0303949 A1 | 11/2013 | Kawaguchi et al. |
| 2015/0250496 A1 | 9/2015 | Kawaguchi et al. |

FOREIGN PATENT DOCUMENTS

| | | |
|---|---|---|
| JP | 2013085954 A | 5/2013 |
| JP | 2013220109 A | 10/2013 |
| JP | 2013545534 A | 12/2013 |
| JP | 2014121618 A | 7/2014 |
| JP | 2014515652 A | 7/2014 |
| WO | 2012061643 A1 | 5/2012 |
| WO | 2012128362 A1 | 9/2012 |

OTHER PUBLICATIONS

International Search Report (ISR) dated Mar. 7, 2017 issued in International Application No. PCT/JP2016/087275.
Written Opinion dated Mar. 7, 2017 issued in International Application No. PCT/JP2016/087275.

* cited by examiner

SURGICAL INSTRUMENT AND CONNECTOR

CROSS-REFERENCE TO RELATED APPLICATION

This application is a continuation of PCT International Application No. PCT/JP2016/087275 filed on Dec. 14, 2016 which claims the benefit of priority from Japanese Patent Application No. 2015-254881, filed on Dec. 25, 2015, the entire contents of which are incorporated herein by reference.

BACKGROUND

The present disclosure relates to a surgical instrument and a connector.

In the related art, a surgical instrument to make an incision, excision, or cauterization of tissues by transferring ultrasonic waves or high frequency waves by a probe to a treatment tool that is arranged at an end of a handpiece has been used.

When using this kind of surgical instrument, it is necessary to perform incision of tissues by rotating the treatment tool. An ultrasound transducer that is detachably arranged at a handpiece has a cable connecting the ultrasound transducer and an ultrasonic output device. To prevent entanglement of the cable at the time of rotating the treatment tool, the ultrasound transducer is attached rotatably to the handpiece (For example, refer to Japanese Laid-open Patent Publication No. 2014-121618 and International Publication Pamphlet No. 2012/128362).

SUMMARY

A surgical instrument according to one aspect of the present disclosure includes: a handpiece; a movable member configured to transmit a driving force to a treating member to treat a subject by moving relatively to the handpiece; and a connector arranged inside the handpiece, and including a strip to apply a pressing force to the movable member, wherein the movable member includes a first conductive portion formed therein, the connector includes a second conductive portion formed on the strip, the second conductive portion abutting against the first conductive portion to connect the movable member and the handpiece electrically, and the second conductive portion of the connector is a molded interconnect device constituting a three-dimensional circuit.

A connector for surgical instrument according to another aspect of the present disclosure includes: a transducer including an ultrasonic oscillator driven by ultrasonic vibrations; a ring portion in which an insertion portion of the transducer is inserted; a strip configured to apply a pressing force to the insertion portion inserted in the ring portion; and a second conductive portion provided in the strip, and configured to abut against a first conductive portion provided in the insertion portion of the transducer when the insertion portion of the transducer is inserted inside to be electrically connected with the first conductive portion, wherein the second conductive portion is a molded interconnect device constituting a three-dimensional circuit.

A connector for surgical instrument according to still another aspect of the present disclosure includes: a bipolar treatment tool; a strip configured to press two pieces of driving members made from a conductive material from inside to outside of the two pieces of driving members; and a second conductive portion provided in the strip, and configured to abut against the two pieces of driving members serving as a first conductive portion to be electrically connected therewith, wherein the second conductive portion is a molded interconnect device constituting a three-dimensional circuit.

The above and other features, advantages and technical and industrial significance of this disclosure will be better understood by reading the following detailed description of presently preferred embodiments of the disclosure, when considered in connection with the accompanying drawings.

DETAILED DESCRIPTION

In the following explanation, an ultrasonic surgical apparatus and a bipolar treatment tool are explained as forms to implement the present disclosure (hereinafter, "embodiments"). The embodiments are not intended to limit the present disclosure. Furthermore, like reference symbols are assigned to like parts throughout the drawings. Moreover, the drawings are schematic illustration, and it should be noted that a relationship between thickness and width of each member, a ratio of each member, and the like are different from actual situations. In addition, sizes and ratios may be different from each other among the drawings also.

First Embodiment

Figure 1:
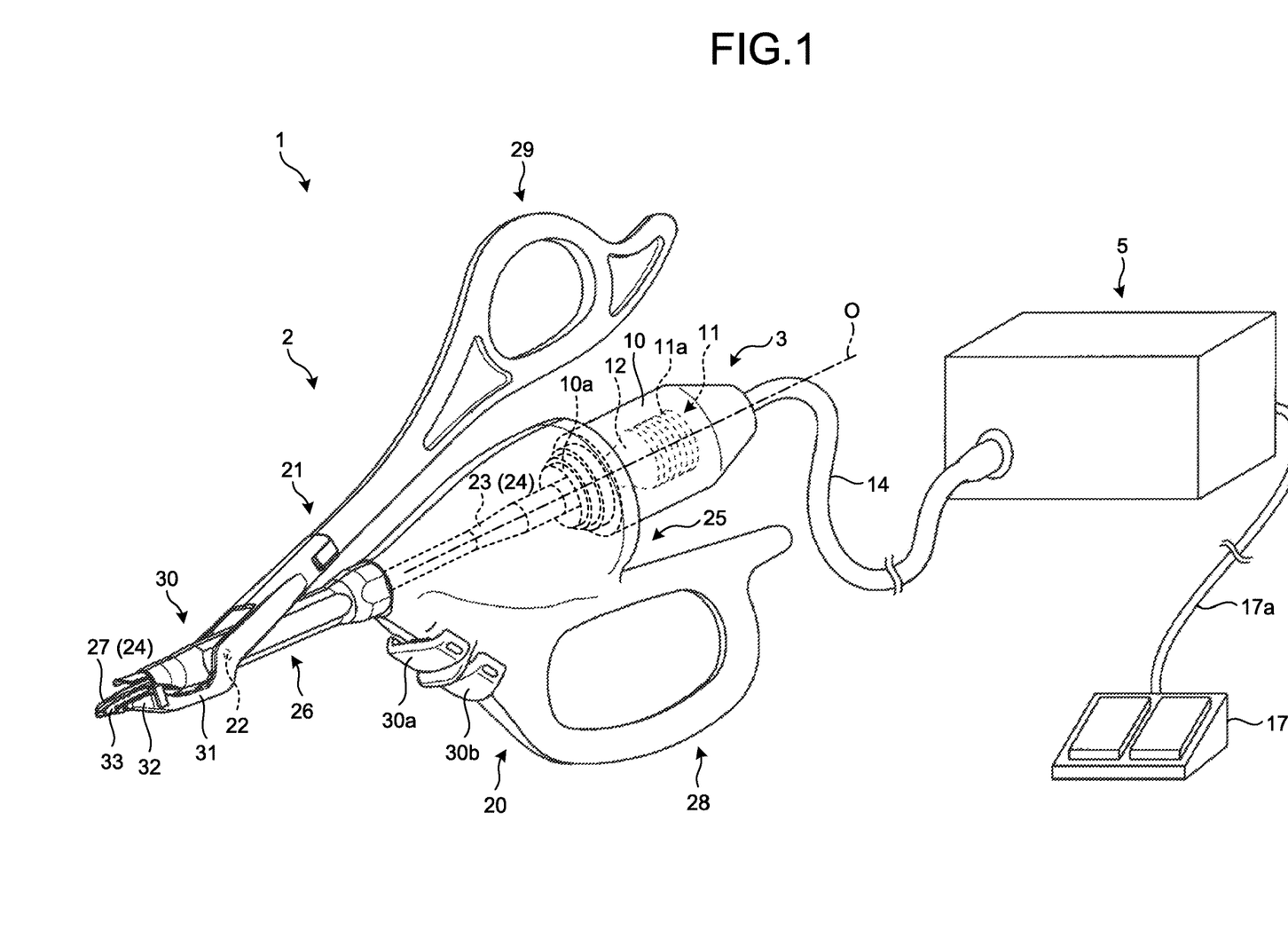
FIG. 1 illustrates a configuration of an ultrasonic surgical apparatus according to a first embodiment.
Figure 2:
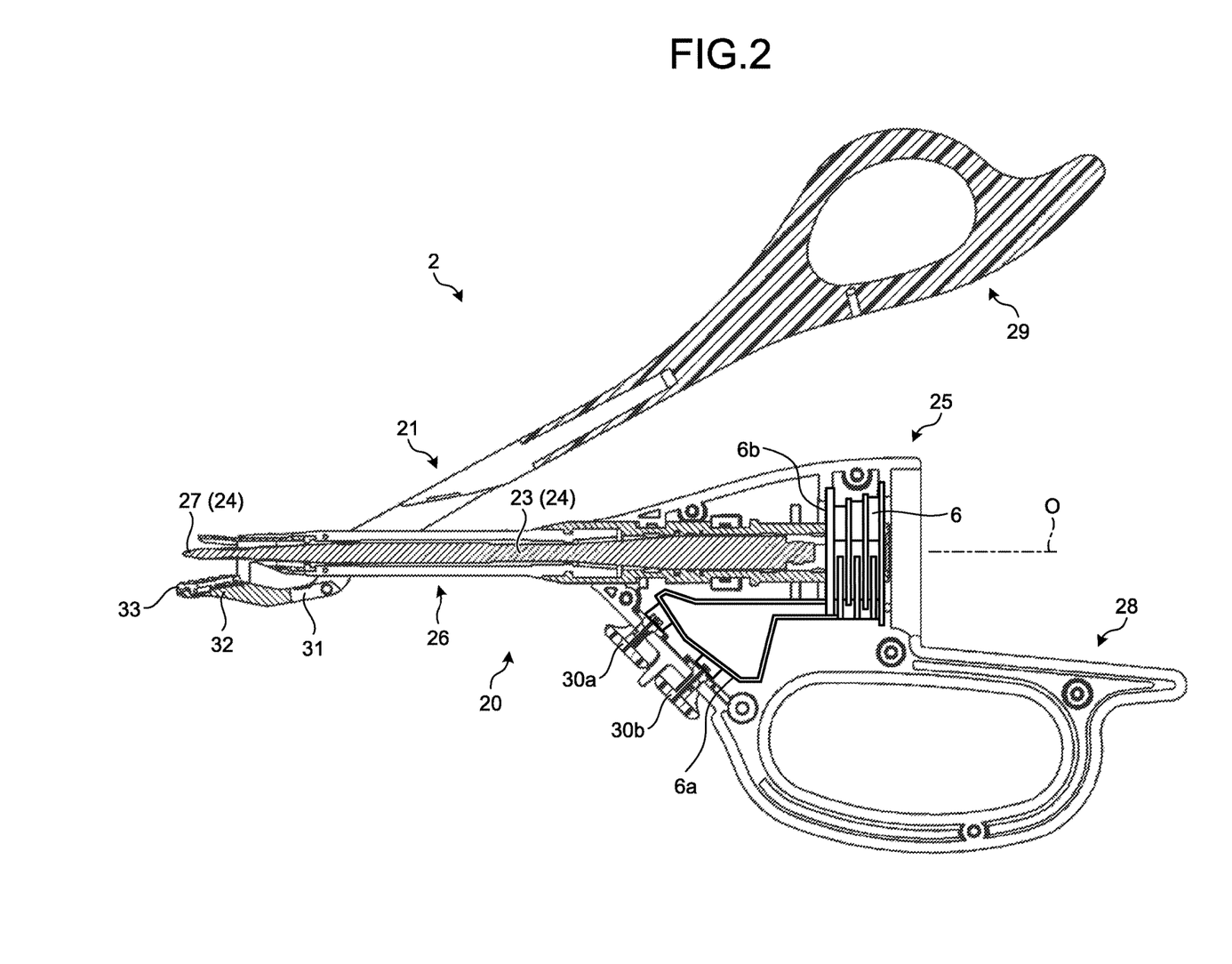
FIG. 2 is a cross-section of an ultrasonic surgical instrument in FIG. 1.

FIG. 1 illustrates a configuration of an ultrasonic surgical apparatus 1 according to a first embodiment. FIG. 2 is a cross-section of an ultrasonic surgical instrument in FIG. 1. An ultrasonic surgical apparatus according to the first embodiment includes a handpiece 2 that is held by an operator, an ultrasound transducer (movable member) 3 that is attached to the handpiece 2, and an output control device 5 to which the ultrasound transducer 3 is connected through a cable 14.

The ultrasound transducer 3 includes an ultrasonic oscillator 11 that is provided inside an oscillator cover 10 in a substantially cylindrical shape. In the first embodiment, the ultrasonic oscillator 11 is structured by arranging plural piezoelectric devices 11a in a ring shape in a direction of longitudinal axis of the oscillator cover 10. Furthermore, to an insertion portion of the ultrasonic oscillator 11, a base end portion of a horn 12 to increase amplitude of ultrasonic vibrations is connected. Moreover, the horn 12 is fixed inside the oscillator cover 10 through an insulating member 10c (refer to FIG. 4), and a tip end portion of the horn 12 protrudes out of an insertion portion 10a to outside.

The cable 14 extends from a base end side of the oscillator cover 10 of the ultrasound transducer 3, and the ultrasound transducer 3 is connected to the output control device 5 through the cable 14. To the output control device 5, a footswitch 17 to turn on and off the output of a driving signal according to an output mode is connected through a cable 17a.

The handpiece 2 is constituted of forcep-shaped (scissor-shaped) treatment tool including a handpiece main body 20 that includes therein a waveguide member 23 that transmits ultrasonic vibrations from a base end side at which the ultrasound transducer 3 is attached to a tip end side, and a clamp arm 21 that is pivotally (rotatably) supported with its axis by the handpiece main body 20 through an axis 22.

The handpiece main body 20 includes a housing 25 in a substantially conical shape, and a sheath 26 that is held in this housing 25.

The housing 25 is, for example, a pair of resin mold housing members separated into a left part and a right part, connected to each other by a chemical means or a mechanical means. Furthermore, a first finger handle 28 is formed at an offset position from a center axis O of the housing 25 on the base end side of the housing 25 integrally therewith. On a side of the first finger handle 28 facing the center axis O, a connector 6 to connect the insertion portion 10a of the ultrasound transducer 3 detachably is arranged.

Moreover, at a front end portion of the first finger handle 28 of the housing 25, two switch buttons 30a, 30b are provided. These switch buttons 30a, 30b are arranged at a position facing an index finger (and a middle finger), for example, when an operator put a middle finger and a ring finger, or a ring finger and a little finger into the first finger handle 28, and by pressing the switch buttons 30a, 30b, the operator inputs operations. On an inner circumference side of the housing 25 on which the switch buttons 30a, 30b are arranged, switch portions 6f-1, 6f-2 of the connector 6 are arranged (refer to FIG. 3C and FIG. 3E), and the switch portion 6f-1 is switched between open and closed by an input operation with the switch button 30a. Similarly, the switch portion 6f-2 is switched between open and closed by an input operation with the switch button 30b.

The sheath 26 is mostly inserted in the housing 25, and a part thereof extends to outside of the housing 25. Inside the sheath 26, the waveguide member 23 made from conductive metal is held through an elastic member (not illustrated) such as a rubber ring, a plastic member, or a flange formed by increasing the diameter of a part of the waveguide member 23.

A base side of the sheath 26 is arranged in the connector 6, and into an inside of the sheath 26 on the base side, the tip end portion of the horn 12 protruding out of the insertion portion 10a is inserted when the insertion portion 10a of the ultrasound transducer 3 is connected to the connector 6. The tip end portion of the horn 12 is connectable to a base end side of the waveguide member 23 by being screwed or the like. By this connection, the horn 12 and the waveguide member 23 are acoustically and electrically connected to each other. Thus, to the waveguide member 23, ultrasonic vibrations generated by the ultrasonic oscillator 11 of the ultrasound transducer 3 are transmitted, and a high-frequency electric current (drive signal) output from the output control device 5 is transmitted. The ultrasound transducer 3 is attached rotatably relative to the housing 25 in terms of preventing entanglement of the cable 14.

On the other hand, on a tip end side of the sheath 26, an outer diameter thereof decreases, and an ultrasound probe 27 that is provided at a tip end portion of the waveguide member 23 protrudes from a tip end of the sheath 26 with the decreased outer diameter. In the first embodiment, the ultrasound probe 27 is integrally formed with the waveguide member 23 from conductive metal, and the waveguide member 23 and the ultrasound probe 27 constitute a probe unit 24.

The ultrasound probe 27 is curved in a J-shape at its tip end. In the first embodiment, the ultrasound probe 27 has a function as a first electrode unit to transmit high-frequency current to tissue in addition to a function of transmitting ultrasonic vibrations to tissues.

The clamp arm 21 is constituted of a rod-shaped member formed with a pair of arms separated into a left part and a right part, connected to each other by a chemical means or a mechanical means. A concave portion is arranged in a middle of the arm member, and this concave portion forms an opening 30 that extends in a direction of length of the clamp arm 21. To this opening 30, the tip end side of the sheath 26 is inserted, and joined such that an inner side of the opening 30 and an outer side of the sheath 26 are connected through the axis 22, the clamp arm 21 is pivotally (rotatably) supported with respect to the handpiece main body 20.

On a base end side of the clamp arm 21, a second finger handle 29 that pairs off with the first finger handle 28 provided on the handpiece main body 20 is formed in a continuous manner. The second finger handle 29 is structured, for example, in a ring shape suitable for inserting a thumb of an operator or the like. For example, by moving a finger (for example, a ring finger and a little finger) inserted in the first finger handle 28 and a finger (for example, a thumb) inserted in the second finger handle 29 relative to each other by an operator or the like, the clamp arm 21 pivotally moved about the axis 22.

On the other hand, on a tip end side of the clamp arm 21 that intersects with the handpiece main body 20 through the axis 22, a curved portion 31 to avoid interference with the sheath 26 when the clamp arm 21 is pivotally moved is provided. Furthermore, on a tip end side of this curved portion 31, a base 32 that opposes to the ultrasound probe 27 is provided. On this base 32, a jaw 33 made from conductive metal is arranged.

Figure 3A:
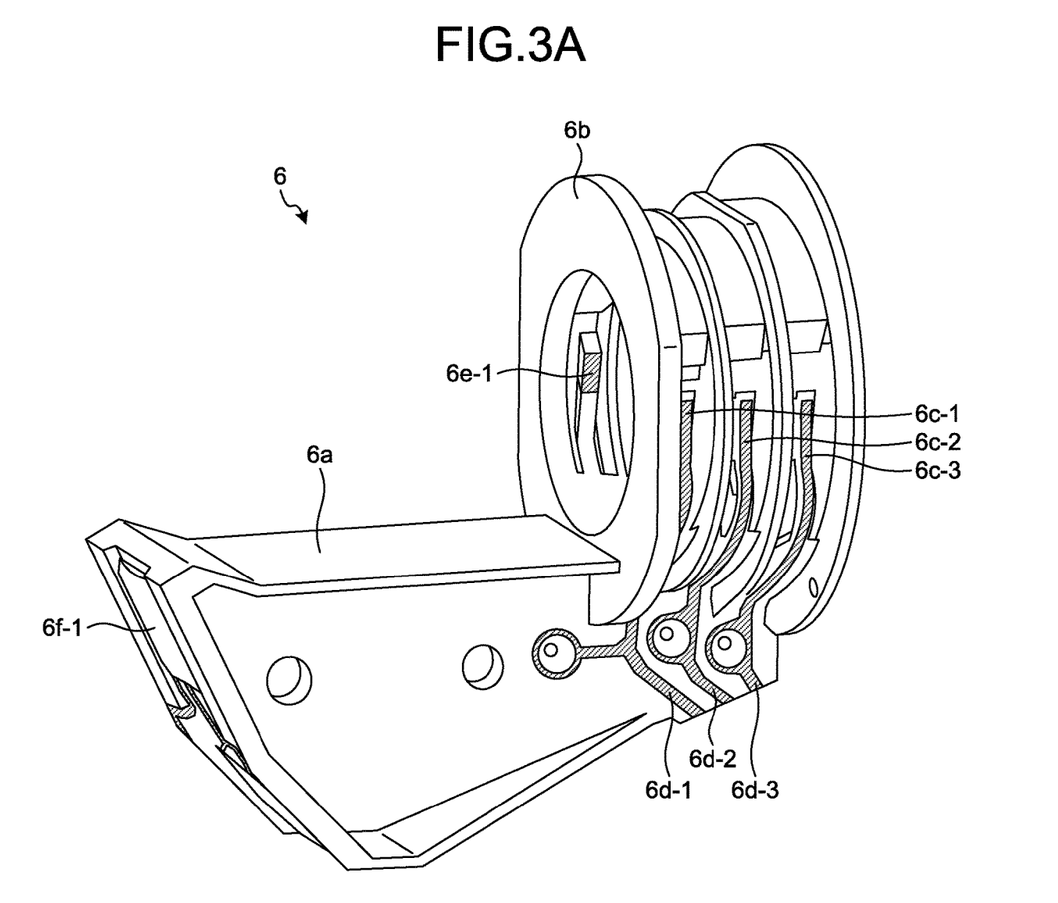
FIG. 3A is a perspective view of a connector that is used for the ultrasonic surgical instrument in FIG. 1.
Figure 3B:
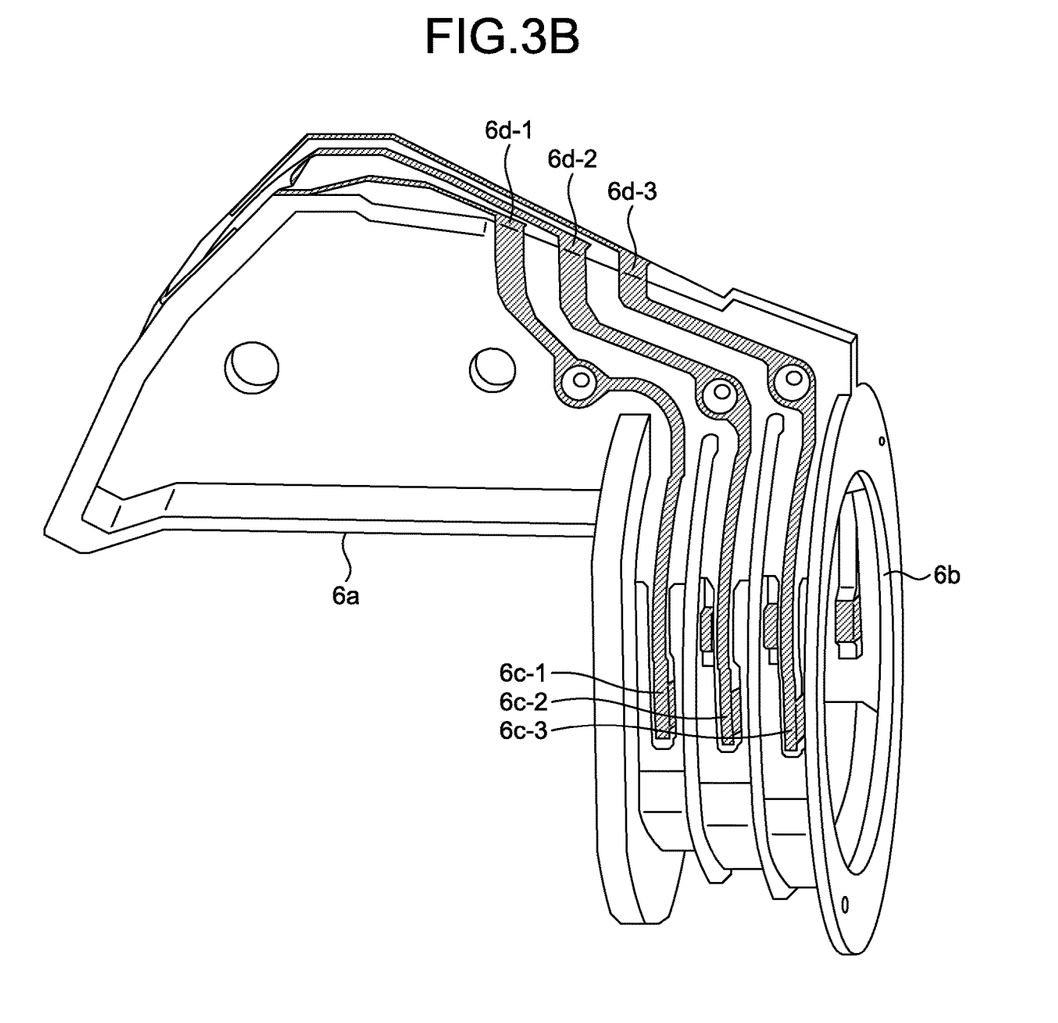
FIG. 3B is a perspective view of the connector in FIG. 3A viewed from another direction (a ring portion side).
Figure 3C:
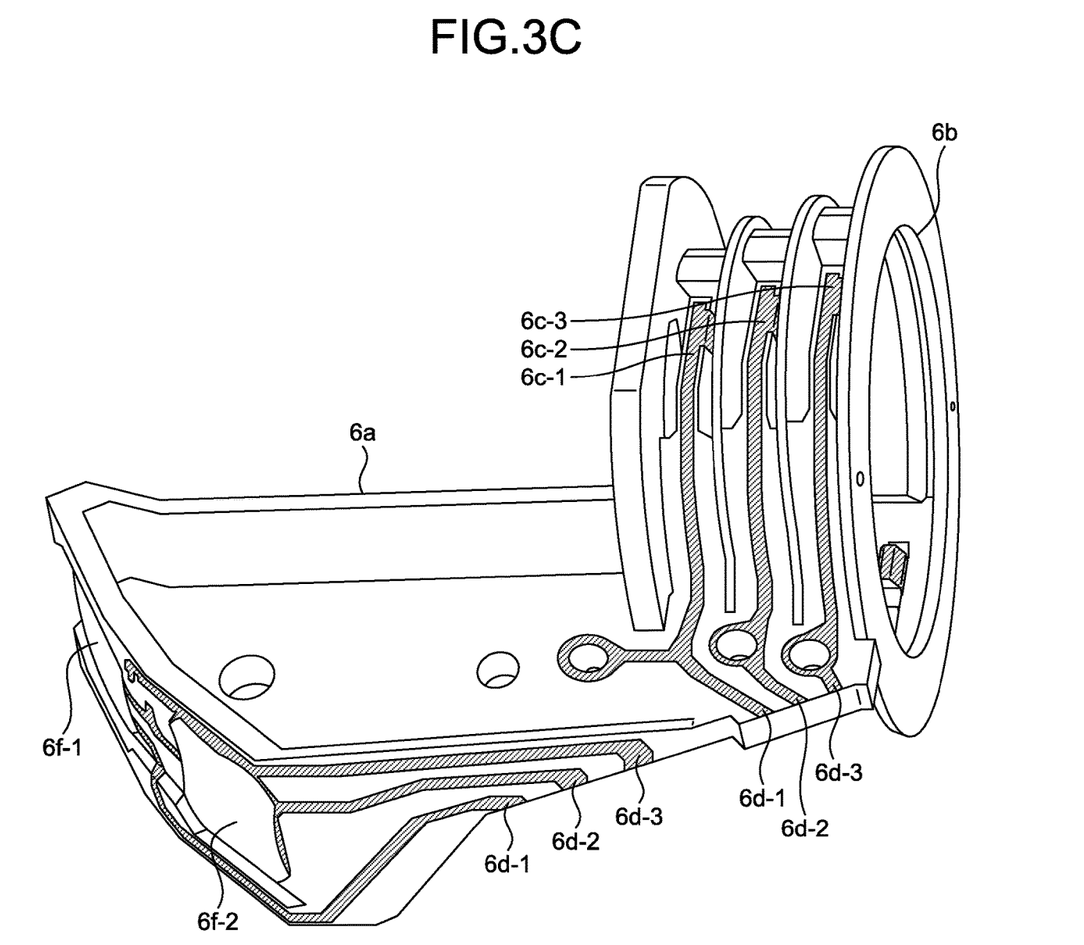
FIG. 3C is a perspective view of the connector in FIG. 3A viewed from another direction (a metallic wiring side).
Figure 3D:
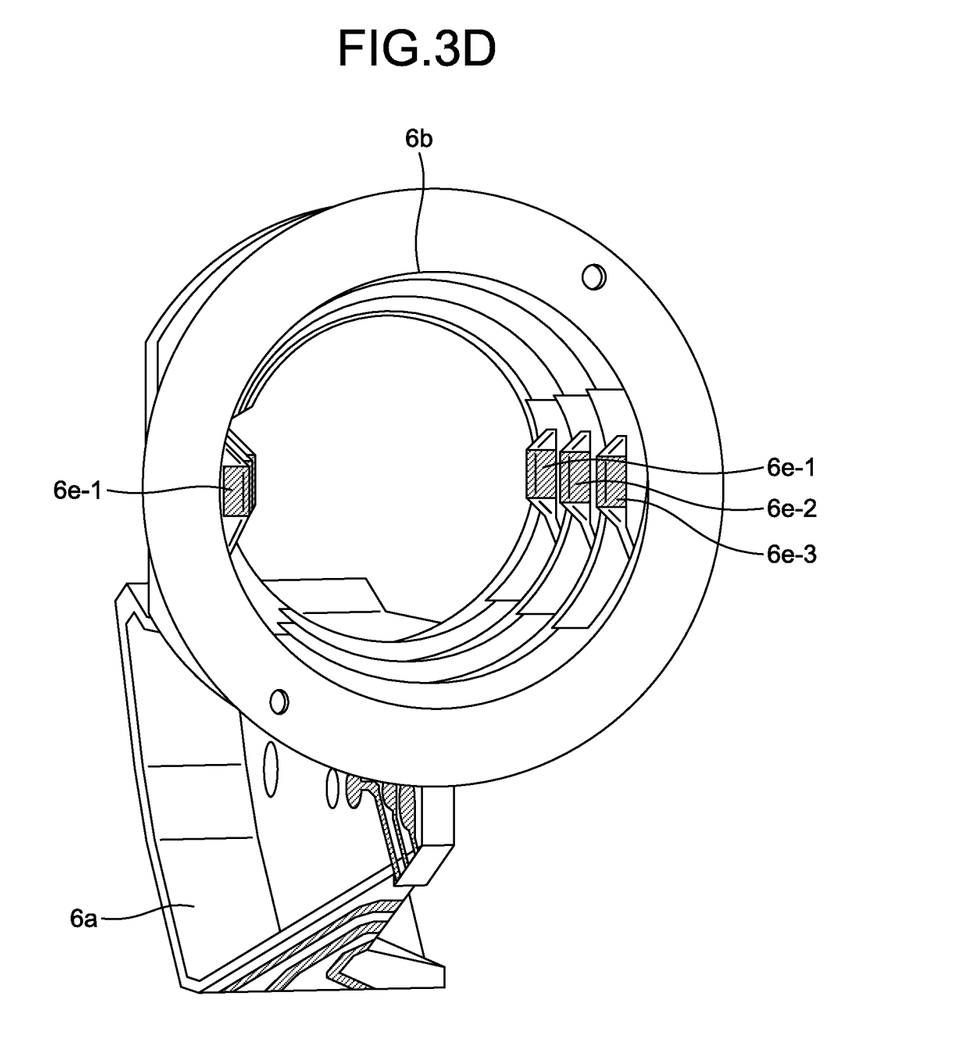
FIG. 3D is a perspective view of the connector in FIG. 3A viewed from another direction (a transducer insertion side of the ring portion).
Figure 3E:
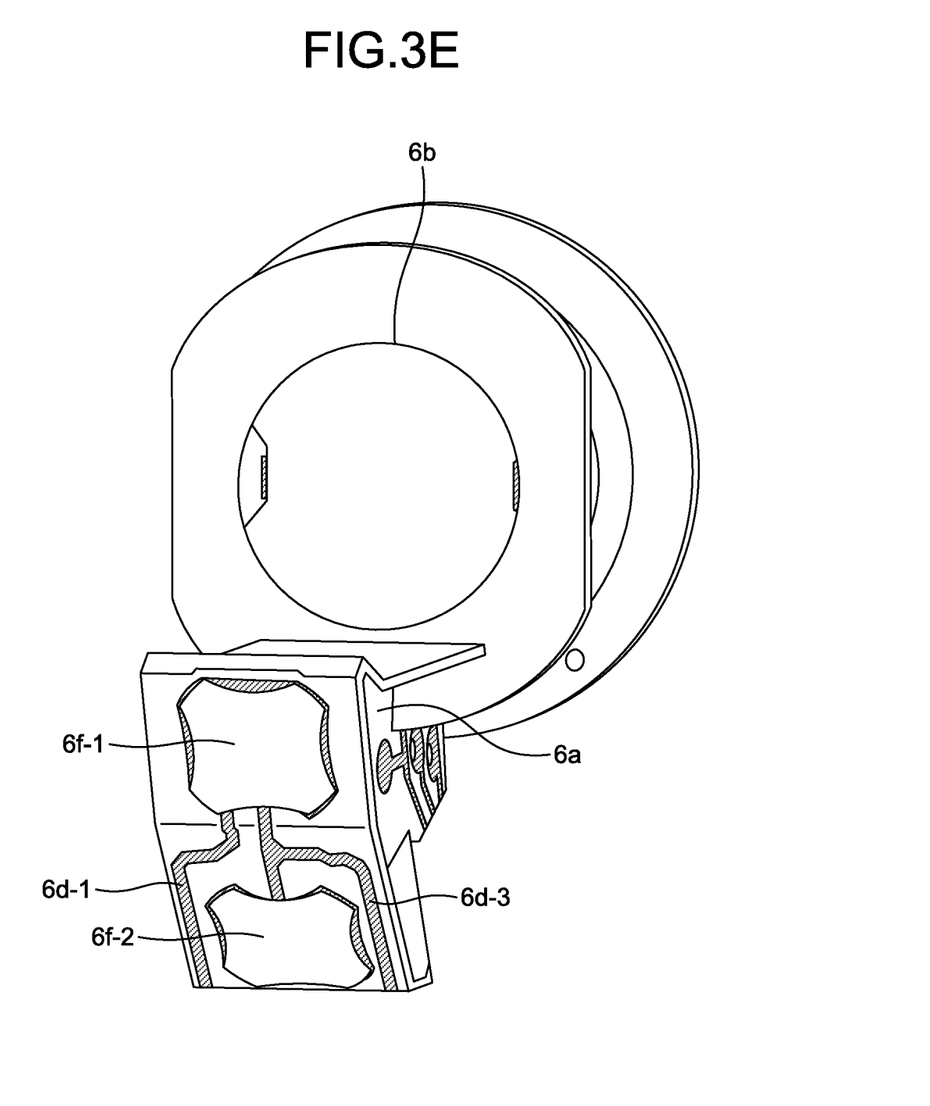
FIG. 3E is a perspective view of the connector in FIG. 3A viewed from another direction (a switch unit side).
Figure 4:
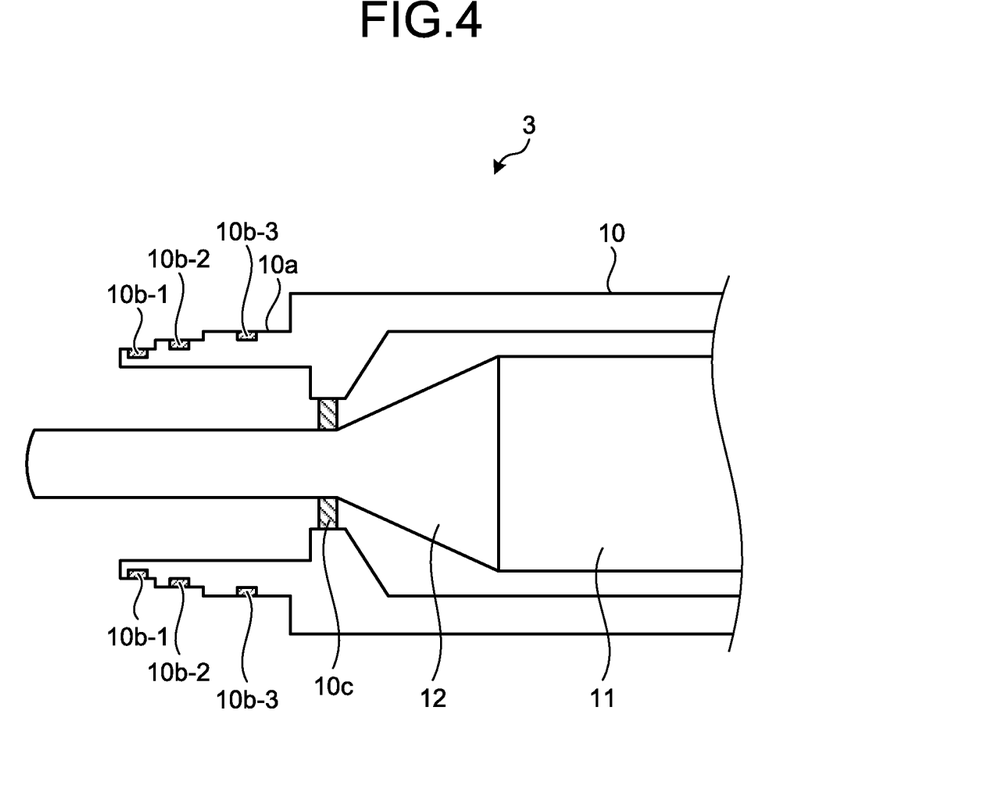
FIG. 4 is a cross-section of an insertion portion of an ultrasound transducer.

Next, the connector 6 according to the first embodiment and connection between the connector 6 and the ultrasound transducer 3 are explained referring to the drawings. FIG. 3A is a perspective view of the connector 6 that is used for the ultrasonic surgical instrument 1 in FIG. 1. FIG. 3B is a perspective view of the connector 6 viewed from a ring portion side. FIG. 3C is a perspective view of the connector 6 viewed from a metallic wiring side. FIG. 3D is a perspective view of the connector 6 viewed from a transducer insertion side of the ring portion. FIG. 3E is a perspective view from a switch unit side. FIG. 4 is a cross-section of the insertion portion 10a of the ultrasound transducer 3.

The connector 6 includes a connector main body 6a, a ring portion 6b to which the insertion portion 10a of the oscillator cover 10 of the ultrasound transducer 3 is inserted, strips 6c-1, 6c-2, 6c-3 that apply a pressing force to the insertion portion 10a inserted into the ring portion 6b, second conductive portions 6e-1, 6e-2, 6e-3, third conductive portions 6d-1, 6d-2, 6d-3, and the switch portions 6f-1, 6f-2.

The strips 6c-1, 6c-2, 6c-3 have an arc shape. The strips 6c-1, 6c-2, 6c-3 are supported by the ring portion 6b on a base end side of the arc shape, and press the insertion portion 10a of the ultrasound transducer 3 on a tip end side of the arc shape. On an inner circumference side of the strips 6c-1, 6c-2, 6c-3, the second conductive portions 6e-1, 6e-2, 6e-3 are formed. The strips 6c-1, 6c-2, 6c-3 are formed on both sides of the ring portion 6b to be paired such that the second conductive portions 6e-1, 6e-2, 6e-3 are symmetrical about a center of the ring portion 6b.

on a side of the connector main body 6a, the side in contact with the inner circumference side of the housing 25, the switch portions 6f-1, 6f-2 are provided. The switch portions 6f-1, 6f-2 are switched between open and closed by an input operation with the switch buttons 30a, 30b.

The third conductive portions 6d-1, 6d-2, 6d-3 are formed so as to extend from the tip end side of the arc shape toward the base end side on a surface facing to a surface on which the second conductive portions 6e-1, 6e-2, 6e-3 are formed out of surfaces of the strips 6c-1, 6c-2, 6c-3. By arranging the third conductive portions 6d-1, 6d-2, 6d-3 on the surface opposing to the surface on which the second conductive portions 6e-1, 6e-2, 6e-3 are formed, that is, on an outer circumference side of the strips 6c-1, 6c-2, 6c-3, it is possible to prevent a break of wire even when the strips 6c-1, 6c-2, 6c-3 are pushed up as a result of insertion of the ultrasound transducer 3 into the ring portion 6b. The third conductive portions 6d-1, 6d-2, 6d-3 are a wiring unit that connects the third conductive portions 6d-1, 6d-2, 6d-3 and the second conductive portions 6e-1, 6e-2, 6e-3. The third conductive portion 6d-1 electrically connect the switch portion 6f-1 and the second conductive portion 6e-1. The third conductive portion 6d-2 electrically connect the switch portion 6f-2 and the second conductive portion 6e-2. The third conductive portion 6d-3 electrically connect the switch portions 6f-1, 6f-2 and the second conductive portion 6e-3. The third conductive portion 6d-3 is a ground of the switch portions 6f-1, 6f-2.

Moreover, as illustrated in FIG. 4, on an outer circumference of the insertion portion 10a of the ultrasound transducer 3 that is inserted into the ring portion 6b of the connector 6, first conductive portions 10b-1, 10b-2, 10b-3 are formed. In a state in which the ultrasound transducer 3 is inserted in the connector 6, the first conductive portion 10b-1 comes in contact with the second conductive portion 6e-1, the first conductive portion 10b-2 comes in contact with the second conductive portion 6e-2, and the first conductive portion 10b-3 comes in contact with the second conductive portion 6e-3.

As described above, the switch button 30a, the switch portion 6f-1, the third conductive portion 6d-1, the second conductive portion 6e-1, and the first conductive portion 10b-1 structure an independent first electrical-signal circuit to the output control device 5 through a not illustrated electrical signal line in the cable 14. Furthermore, the switch button 30b, the switch portion 6f-2, the third conductive portion 6d-2, the second conductive portion 6e-2, and the first conductive portion 10b-2 structure an independent second electrical-signal circuit to the output control device 5 through a not illustrated electrical signal line in the cable 14. Moreover, the switch portions 6f-1, 6f-2, the third conductive portion 6d-3, the second conductive portion 6e-3, and the first conductive portion 10b-3 structure an independent ground circuit to the output control device 5 through a not illustrated electrical signal line in the cable 14.

When the switch button 30a is pressed, the switch portion 6f-1 is closed, and the first electrical-signal circuit and the ground circuit are electrically connected by the switch portion 6f-1. Thus, an electrical signal is transmitted from the switch portion 6f-1 to the output control device 5. Subsequently, for example, upon supplying an electric current to the ultrasonic oscillator 11 through the electrical signal line from an ultrasound control unit in the output control device 5 to generate ultrasonic vibrations by the ultrasonic oscillator 11, it is turned to a state in which a high-frequency current control unit in the output control device 5 outputs a high frequency current. Furthermore, when the switch button 30b is pressed, the switch portion 6f-2 is closed, and the second electrical-signal circuit and the ground circuit are electrically connected by the switch portion 6f-2. Thus, an electrical signal is transmitted from the switch portion 6f-2 to the output control device 5. Thus, for example, it is turned into a state in which only a high frequency current is output from the high-frequency current control unit, but no ultrasonic vibrations are generated.

The connector 6 is a molded interconnect device (MID) in which the second conductive portions 6e-1, 6e-2, 6e-3, the third conductive portions 6d-1, 6d-2, 6d-3, and the switch portions 6f-1, 6f-2 constitute a three-dimensional circuit. As the second conductive portions 6e-1, 6e-2, 6e-3, the third conductive portions 6d-1, 6d-2, 6d-3, and the switch portions 6f-1, 6f-2 are subjected to laser irradiation and then to plating to be formed integrally, no electrical connection is present inside the connector 6, and reliable electrical continuity is achieved. On the other hand, the connector main body 6a, the ring portion 6b, and the strips 6c-1, 6c-2, 6c-3 are made from a resin material to which injection molding may be applied. The strips 6c-1, 6c-2, 6c-3 are preferable to be made from resin with a bending elastic modulus of 1000 MPa to 5000 MPa not to interfere rotation of the ultrasound transducer 3 while enabling application of a pressing force to the strips 6c-1, 6c-2, 6c-3. In addition, to prevent cracks due to loads of repeated attachment and detachment, or the like, it is preferable to be made from resin with an yield strain of 3% or higher.

Conventionally, transmission of an electrical signal between the switch buttons 30a, 30b and the ultrasound transducer 3 has been done by engaging an independent conductive ring (corresponding to the second conductive portion and the third conductive portion) with a connector, and by connecting a control board on which a switch unit is formed and the connector by a flexible substrate. In the first embodiment, transmission of an electrical signal between the switch buttons 30a, 30b and the ultrasound transducer 3 may be performed by the connector 6 being an MID and, therefore, a manufacturing process of the handpiece 2 may be simplified and manufacturing costs may be reduced.

Figure 5A:
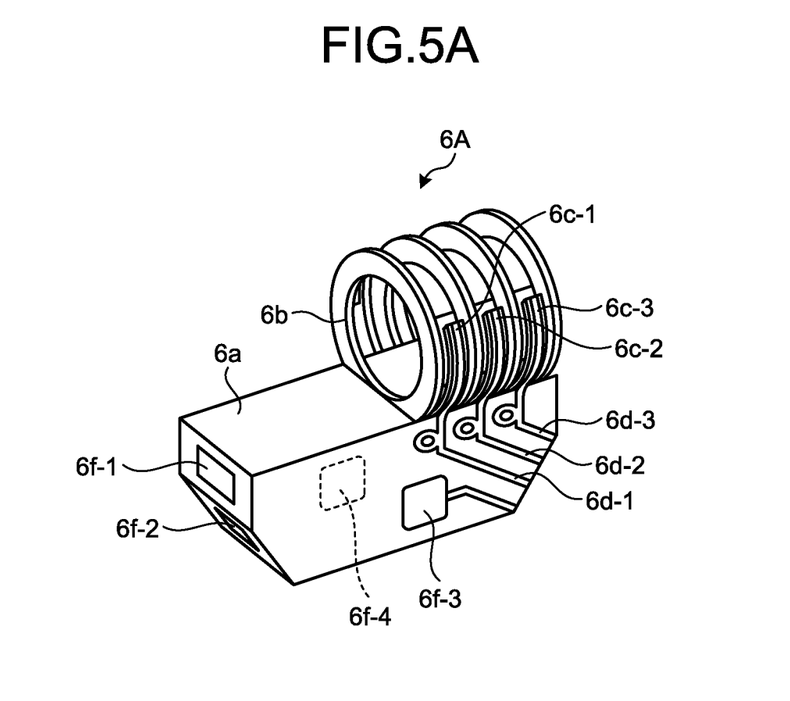
FIG. 5A is a perspective view of a connector according to a first modification of the first embodiment.
Figure 5B:
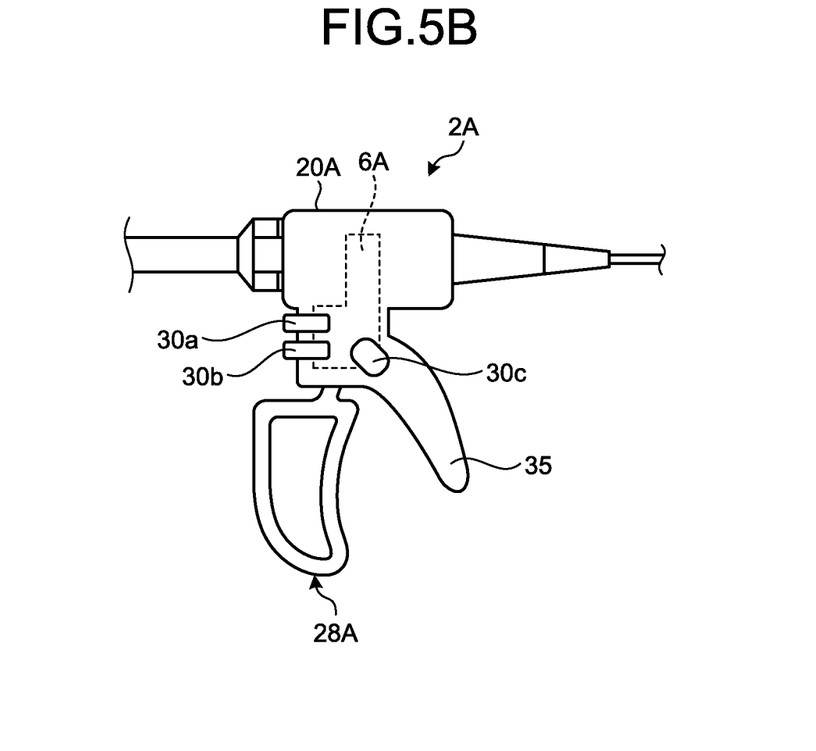
FIG. 5B illustrates arrangement of the connector of FIG. 5A inside a handpiece.

Although one of an inline grip has been explained as an example of the handpiece 2 in the first embodiment, it is not limited thereto, and is also applicable to one of a front drive grip. In the following, a connector that is used in a handpiece with a front drive grip is explained. FIG. 5A is a perspective view of a connector according to a first modification of the first embodiment. FIG. 5B illustrates arrangement of the connector of FIG. 5A inside a handpiece.

As illustrated in FIG. 5B, in a front drive grip handpiece 2A according to the first modification, the switch buttons 30a, 30b are arranged above a first finger handle 28A of the handpiece main body 20A, and switch buttons 30c, 30d (not illustrated) are arranged near a base end portion of a grip 35.

A connector 6A has four switch portions 6f-1, 6f-2, 6f-3, 6f-4 in the connector main body 6a. The switch portions 6f-1, 6f-2 are formed at positions to be abut against the switch buttons 30a, 30b, respectively when the switch buttons 30a, 30b are pressed, and the switch portions 6f-3, 6f-4 are formed at positions to be abut against the switch buttons 30c, 30d, respectively, when the switch buttons 30c, 30d are pressed. The switch portions 6f-1, 6f-2, 6f-3, and 6f-4 are switched between open and closed when the switch buttons 30a, 30b, 30c, 30d are pressed by an operator with a middle finger, an index finger or a thumb.

Figure 6A:
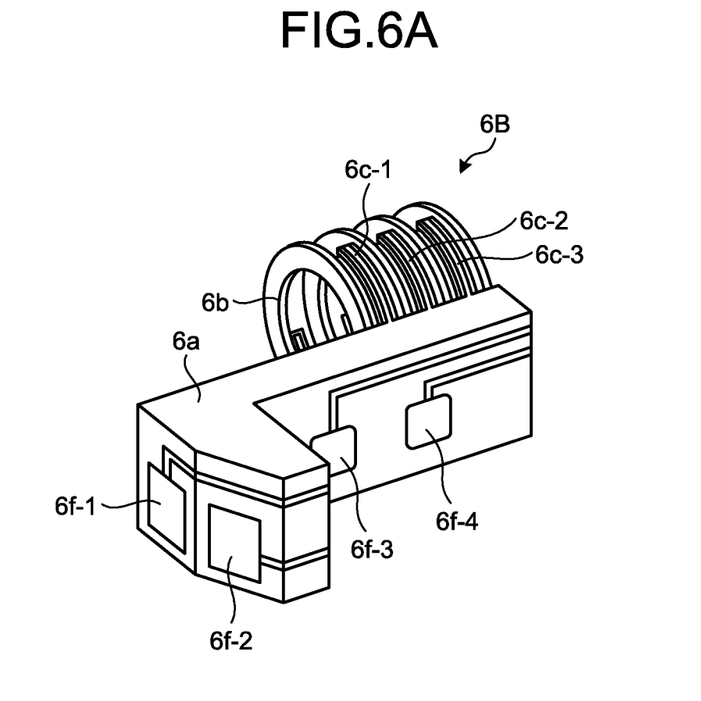
FIG. 6A is a perspective view of a connector according to a second modification of the first embodiment.
Figure 6B:
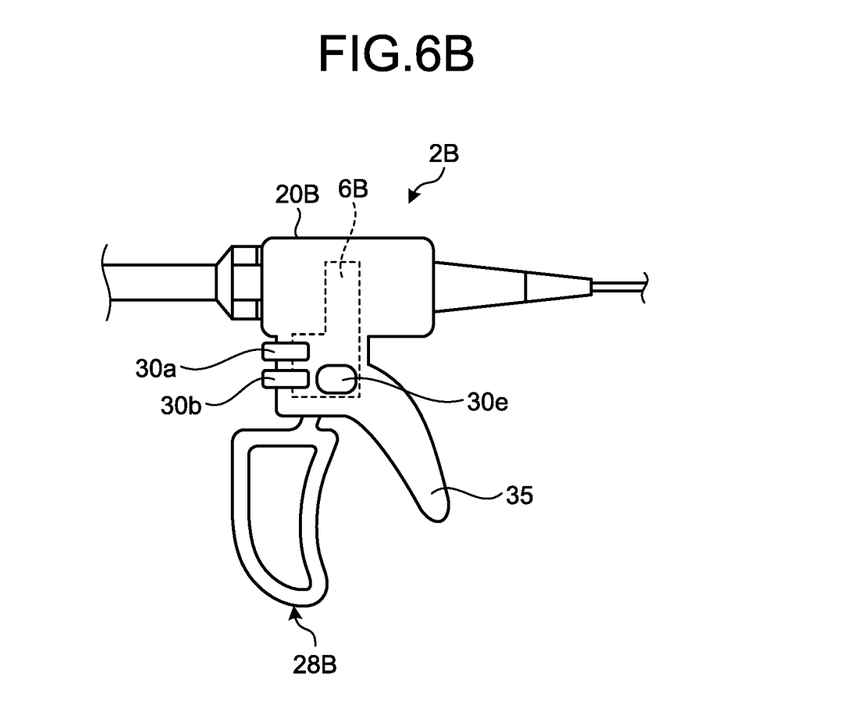
FIG. 6B illustrates arrangement of the connector of FIG. 6A inside the handpiece.

Furthermore, a connector that is used in a front drive grip handpiece may be one of the following kind. FIG. 6A is a perspective view of a connector according to a second modification of the first embodiment. FIG. 6B illustrates arrangement of the connector of FIG. 6A inside the handpiece.

As illustrated in FIG. 6B, in a front drive grip handpiece 2B according to the second modification, the switch buttons 30a, 30b are arranged above a first finger handle 28B of a handpiece main body 20B, and a switch button 30e is arranged on a side close to the base end portion of the grip 35 (position to which a thumb faces when a right-handed operator holds the handpiece 2B).

A connector 6B has the four switch portions 6f-1, 6f-2, 6f-3, 6f-4 in the connector main body 6a. The switch portions 6f-1, 6f-2 are formed at positions to be abut against the switch buttons 30a, 30b, respectively when the switch buttons 30a, 30b are pressed, and the switch portions 6f-3, 6f-4 are formed at positions to be abut against the switch buttons 30e, respectively, when the switch buttons 30e is pressed (at one of right and left ends). The switch portions 6f-1, 6f-2, 6f-3, and 6f-4 are switched between open and closed when the switch buttons 30a, 30b, 30e are pressed by an operator with a middle finger, an index finger, or a thumb.

By forming the connectors 6A and 6B, reliable electrical continuity between the ultrasound transducer and the handpiece 2A or 2B may be achieved. Moreover, also in the front drive grip handpieces 2A and 2B, a manufacturing process may be simplified, and manufacturing costs may be reduced.

Furthermore, also in a pencil type surgical instrument disclosed in Japanese Laid-Open Patent Publication No. 2013-192952, by integrally forming a switch portion and a connector with an MID, reliable electrical continuity may be achieved, and manufacturing costs may be reduced by a simplified manufacturing process.

Second Embodiment

Figure 7A:
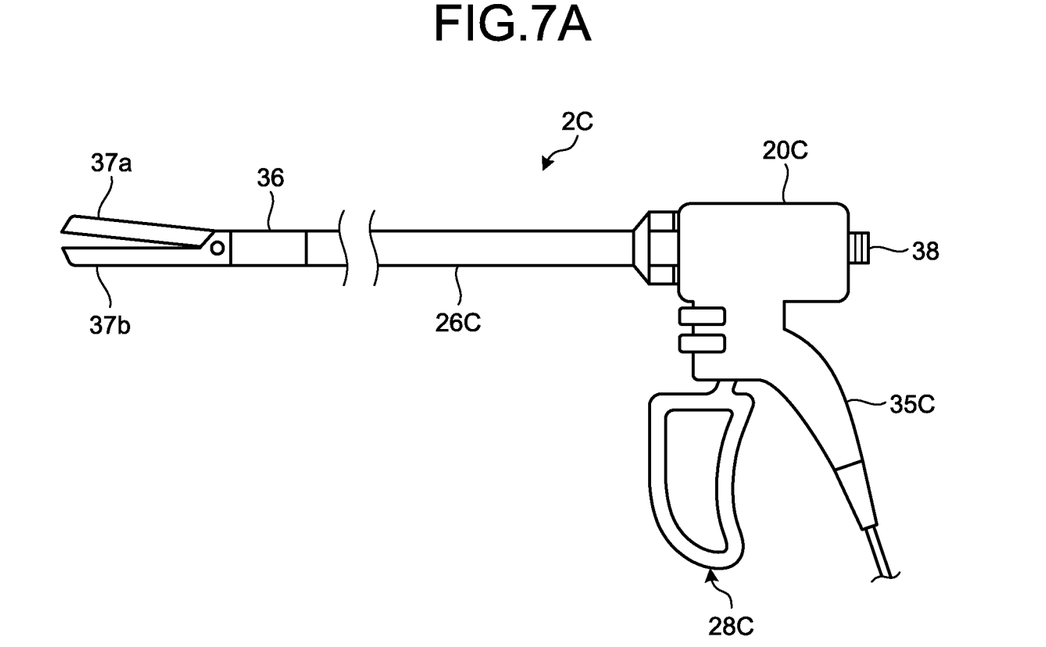
FIG. 7A illustrates a configuration of a bipolar treatment tool according to a second embodiment.
Figure 7B:
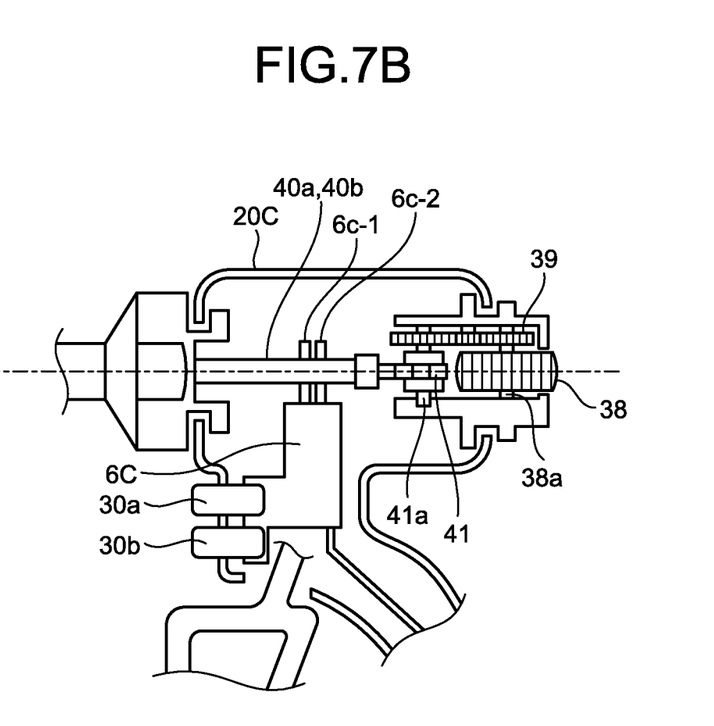
FIG. 7B is a cross-section illustrating a schematic configuration of the bipolar treatment tool of FIG. 7A inside the handpiece.
Figure 7C:
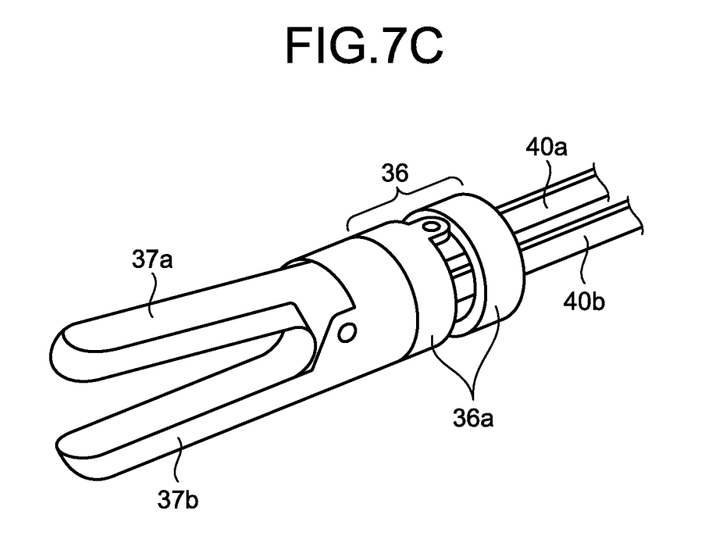
FIG. 7C is an enlarged view of a tip treatment member of the bipolar treatment tool of FIG. 7A.
Figure 7D:
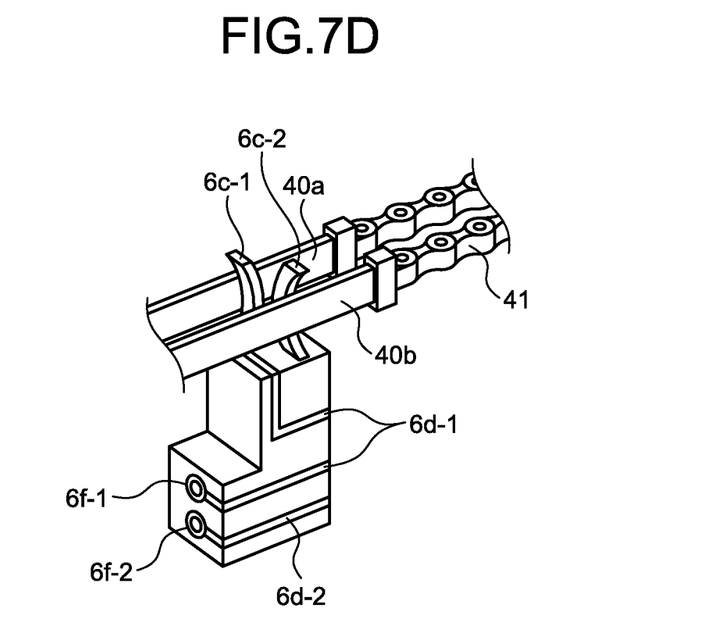
FIG. 7D is an enlarged perspective view of a driving member and proximity of a connector of the bipolar treatment tool.

FIG. 7A illustrates a configuration of a bipolar treatment tool according to a second embodiment. FIG. 7B is a cross-section illustrating a schematic configuration of the bipolar treatment tool of FIG. 7A inside the handpiece. FIG. 7C is an enlarged view of a tip treatment member of the bipolar treatment tool of FIG. 7A. FIG. 7D is an enlarged perspective view of a driving member and proximity of a connector of the bipolar treatment tool. The bipolar treatment tool has two pieces of insulated electric-current supply lines, and performs treatment, such as incision, coagulation, and hemostasis of tissues, through the electric-current supply lines.

A handpiece 2C of the bipolar treatment tool includes a handpiece main body 20C, a first finger handle 28C that is pivotably attached at a lower portion of the handpiece main body 20C, a grip 35C that is integrally formed with the handpiece main body 20C at a lower portion thereof, a sheath 26C that extends out from a tip end side of the handpiece main body 20C, a bending portion 36 of the sheath 26C on a tip end side, and gripping portions 37a, 37b.

In the handpiece 2C, by turning a dial 38, rotation about an axis 38a of the dial 38 is transferred through a gear 39 to be rotation about an axis 41a of a chain 41. The rotation of the chain 41 is converted into forward/backward movement of two pieces of driving members (movable members) 40a, 40b made from a conductive material in the sheath 26C. A wire may be used instead of the chain 41. The two pieces of driving members 40a, 40b and the gripping portions 37a, 37b constitute an electric-current supply line.

Tip ends of the driving members 40a, 40b are inserted into a piece 36a constituting the bending portion 36 on its base end side, and is fixed to the piece 36a on a tip end side. By forward/backward movement of the driving members 40a, 40b by turning of the dial 38, the bending portion 36 is bent.

A connector 6C includes the strips 6c-1, 6c-2 that press from an inner side of the two pieces of the driving members 40a, 40b to an outer side, a second conductive portion that is arranged in the strips 6c-1, 6c-2, abuts against the driving members 40a, 40b, to connect the driving members 40a, 40b and the handpiece 2C electrically, the third conductive portions 6d-1, 6d-2, the switch portions 6f-1, 6f-2. The second conductive portion is formed on a side of the strips 6c-1, 6c-2 abutting against the driving members 40a, 40b, although not illustrated in FIG. 7A to FIG. 7D, and is electrically connected with the switch portions 6f-1, 6f-2 through the third conductive portions 6d-1, 6d-2.

The connector 6C enables reliable electrical continuity by pressing force of the strips 6c-1, 6c-2 also during the forward/backward movement of the driving members 40a, 40b to bend the bending portion 36. Furthermore, by forming the connector 6C with an MID, a manufacturing process may be simplified, and manufacturing costs may be reduced also for the handpiece 2C of the bipolar treatment tool.

According to the present disclosure, a driving member (movable member) driving relatively to a handpiece and the handpiece may be electrically connected by a single part and, therefore, the manufacturing process may be simplified, and manufacturing costs may be reduced.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical instrument comprising:
   a handpiece;
   a movable member configured to transmit a driving force to a treating member to treat a subject by moving relatively to the handpiece; and
   a connector arranged inside the handpiece, and including a strip to apply a pressing force to the movable member, wherein:
the movable member includes a first conductive portion formed therein,
the connector includes a second conductive portion formed on the strip, the second conductive portion abutting against the first conductive portion to connect the movable member and the handpiece electrically,
the second conductive portion of the connector comprises a molded interconnect device constituting a three-dimensional circuit,
the strip includes a tip end portion and a base end portion,
the tip end portion has the second conductive portion provided therein, and is formed so as to be movable relative to the base end portion, and
the surgical instrument further comprises a third conductive portion formed on a surface opposing to a surface on which the second conductive portion is formed, from among surfaces of the strip, so as to extend from a tip end side to a base end side of the strip, the third conductive portion being electrically connected with the second conductive portion.

2. The surgical instrument according to claim 1, wherein the connector is made from a resin having a bending elastic modulus of 1000 MPa to 5000 MPa.

3. The surgical instrument according to claim 1, wherein the connector is made from a resin having a yield strain of at least 3%.

4. A surgical instrument comprising:
a handpiece;
a movable member configured to transmit a driving force to a treating member to treat a subject by moving relatively to the handpiece; and
a connector arranged inside the handpiece, and including a strip to apply a pressing force to the movable member, wherein:
the movable member includes a first conductive portion formed therein,
the connector includes a second conductive portion formed on the strip, the second conductive portion abutting against the first conductive portion to connect the movable member and the handpiece electrically,
the second conductive portion of the connector comprises a molded interconnect device constituting a three-dimensional circuit,
the movable member comprises a transducer that includes an ultrasonic oscillator driving by ultrasonic vibrations,
the first conductive portion is provided in an insertion portion of the transducer,
the connector includes a ring portion in which the insertion portion of the transducer is inserted,
the strip comprises a spring member having an arc shape, and is supported by the ring portion at a base end side of the arc shape, and presses the insertion portion of the transducer with a tip end side, and
the surgical instrument further comprises a third conductive portion formed opposing to a surface on which the second conductive portion is formed so as to extend from the tip end side to the base end side of the arc shape, the third conductive portion being electrically connected with the second conductive portion.

5. The surgical instrument according to claim 4, wherein:
the handpiece includes a switch button to input an operation to control driving of the ultrasonic oscillator, and
in the connector, a switch portion that electrically transmits a signal corresponding to the operation input to the switch button to the transducer through the third conductive portion, the second conductive portion, and the first conductive portion is formed at a position abutting against the switch button.

6. The surgical instrument according to claim 4, wherein the transducer is attached so as to be movable relative to the handpiece.

7. The surgical instrument according to claim 4, wherein the connector is made from a resin having a bending elastic modulus of 1000 MPa to 5000 MPa.

8. The surgical instrument according to claim 4, wherein the connector is made from a resin having a yield strain of at least 3%.

9. A connector for a surgical instrument, the connector comprising:
a transducer including an ultrasonic oscillator driven by ultrasonic vibrations;
a ring portion in which an insertion portion of the transducer is inserted;
a strip configured to apply a pressing force to the insertion portion inserted in the ring portion, the strip including a base end portion and a tip end portion formed so as to be movable relative to the base end portion;
a second conductive portion provided at the tip end portion of the strip, and configured to abut against a first conductive portion provided in the insertion portion of the transducer when the insertion portion of the transducer is inserted in the ring portion so as to be electrically connected with the first conductive portion; and
a third conductive portion formed on a surface opposing to a surface on which the second conductive portion is provided, from among surfaces of the strip, so as to extend from a tip end side to a base end side of the strip, the third conductive portion being electrically connected with the second conductive portion,
wherein the second conductive portion comprises a molded interconnect device constituting a three-dimensional circuit.

* * * * *